(12) United States Patent
Kim et al.

(10) Patent No.: US 11,911,014 B2
(45) Date of Patent: Feb. 27, 2024

(54) ARTICULATING STRUCTURE HAVING ELASTIC MEMBER AND TUBE INSERTING DEVICE HAVING THE SAME

(71) Applicant: KOREA INSTITUTE OF SCIENCE AND TECHNOLOGY, Seoul (KR)

(72) Inventors: Keri Kim, Seoul (KR); Seong Il Kwon, Seoul (KR); Jeongryul Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 781 days.

(21) Appl. No.: 17/008,639

(22) Filed: Sep. 1, 2020

(65) Prior Publication Data
US 2021/0085303 A1    Mar. 25, 2021

(30) Foreign Application Priority Data
Sep. 24, 2019 (KR) .......................... 10-2019-0117451

(51) Int. Cl.
*A61B 17/00* (2006.01)
(52) U.S. Cl.
CPC ............ *A61B 17/00234* (2013.01); *A61B 2017/00309* (2013.01); *A61B 2017/00314* (2013.01); *A61B 2017/00331* (2013.01); *A61B 2017/00345* (2013.01)
(58) Field of Classification Search
CPC ............ A61B 2017/00309; A61B 2017/00314
USPC ............................................................ 606/1
See application file for complete search history.

(56) References Cited

U.S. PATENT DOCUMENTS

| | | | |
|---|---|---|---|
| 7,320,700 B2 * | 1/2008 | Cooper | A61B 34/30 600/101 |
| 8,608,648 B2 | 12/2013 | Banik et al. | |
| 9,833,290 B2 | 12/2017 | Jeong et al. | |

FOREIGN PATENT DOCUMENTS

| | | |
|---|---|---|
| EP | 2124800 B1 | 11/2010 |
| JP | 2019195864 A | 11/2019 |
| KR | 10-2012-0056363 A | 6/2012 |
| KR | 10-2013-0139934 A | 12/2013 |
| KR | 10-2018-0102082 A | 9/2018 |
| KR | 101904524 B1 | 10/2018 |
| KR | 1020190103602 A | 9/2019 |

(Continued)

OTHER PUBLICATIONS

Jung-Wook Suh et al., "Design Considerations for a Hyper-Redundant Pulleyless Rolling Joint With Elastic Fixtures," IEEE/ASME Transactions on Mechatronics, Dec. 2015, pp. 2841-2852, vol. 20, No. 6.

*Primary Examiner* — Nadia A Mahmood
(74) *Attorney, Agent, or Firm* — CANTOR COLBURN LLP (57) ABSTRACT

An articulating structure includes a joint unit including a front segment and a rear segment that are connected in series and perform relative rotation with respect to a rotation portion, and an elastic member interposed between the front segment and the rear segment, and a wire that passes through the front segment and the rear segment in a lengthwise direction of the joint unit, wherein the front segment rotates relative to the rear segment in one direction when the wire is pulled rearward, and the elastic member elastically deforms by a pressing force by the rotation of the front segment to provide a force that resists the pressing force.

30 Claims, 8 Drawing Sheets

(56) References Cited

FOREIGN PATENT DOCUMENTS

WO      2012/040445 A1    3/2012
WO      2017/136710 A2    8/2017

\* cited by examiner

ARTICULATING STRUCTURE HAVING ELASTIC MEMBER AND TUBE INSERTING DEVICE HAVING THE SAME

CROSS-REFERENCE TO RELATED APPLICATION

This application claims priority to Korean Patent Application No. 10-2019-0117451, filed on Sep. 24, 2019, and all the benefits accruing therefrom under 35 U.S.C. § 119, the contents of which in its entirety are herein incorporated by reference.

BACKGROUND

1. Field

The present disclosure relates to an articulating structure and a tube inserting device having the same, and more particularly, to an articulating structure with improved motion characteristics using an elastic element and a tube inserting device having the same.

DESCRIPTION OF GOVERNMENT-FUNDED RESEARCH AND DEVELOPMENT

This research is conducted by Digitech, and funded by robotics industry core technology development (R&D) of Korea Evaluation Institute of Industrial Technology, Ministry of Trade, Industry and Energy, Republic of Korea (Development of flexible joint single passage surgical robotic technology based on fluoroscopy-induced endoscopy for transoral and laparoscopic surgery, No. 1415162841).

2. Description of the Related Art

A typical example of a tube inserting device used to perform a predetermined operation by inserting a long hollow tube into a narrow space is microsurgical instruments for minimally invasive surgery.

The minimally invasive surgery is a surgery that is performed through a minimal incision as compared to open surgery, and it has advantages such as small incisions, less or no scars or after effects and fast recovery.

The microsurgical instruments for minimally invasive surgery are used to perform a predetermined operation such as surgery in a narrow space, so its control has been studied so much.

Particularly, suggests have been various types of articulating structures for locally changing the direction of an end effector positioned at the front end of the microsurgical instrument.

It is known that the articulating structure typically has a structure in which a plurality of segments is connected in series, and steering is accomplished by the relative movements of adjacent segments using a wire.

However, in the conventional articulating structure, in which the articulating structure is aligned in a straight line by the action of two symmetrical wires, and the segments are allowed to make relative rotational movements by pulling one of the two wires, when a load applied to the front segment by the wire reaches a certain magnitude, sudden rotation of the front segment, so-called "buckling" occurs.

When buckling occurs, it is difficult to precisely control the articulating structure, and living tissues may be damage by the sudden bending motion.

Additionally, in the conventional articulating structure, each joint bends at a preset angle according to the length at which the wire is pulled (that is to say, the articulating structure bends in only one predefined shape), so it is impossible to steer the tip adaptively to a variety of working environments.

RELATED LITERATURES

Patent Literatures (Patent Literature 1) U.S. Pat. No. 9,833,290

SUMMARY

The present disclosure is designed to solve the above-described problem, and therefore the present disclosure is directed to providing an articulating structure for preventing buckling occurring in the articulating structure and achieving a more accurate, soft and stable bending motion of the articulating structure, and a tube inserting device having the same.

To achieve the above-described object, according to an aspect of the present disclosure, there is provided an articulating structure including a joint unit including a front segment and a rear segment that are connected in series and perform relative rotation with respect to a rotation portion, and an elastic member interposed between the front segment and the rear segment, and a wire that passes through the front segment and the rear segment in a lengthwise direction of the joint unit, wherein the front segment rotates relative to the rear segment in one direction when the wire is pulled rearward, the elastic member elastically deforms by a pressing force by the rotation of the front segment to provide an elastic force that resists the pressing force, and the elastic force and the pressing force are balanced during the action of the pressing force.

According to an embodiment, a plurality of joint units may be connected in series.

According to an embodiment, the rear segment of a front joint unit may become the front segment of a rear joint unit connected thereto.

According to an embodiment, the elastic members of the plurality of joint units may have same or different elastic coefficients.

According to an embodiment, the plurality of joint units may include a plurality of X direction joint units in which the front segment rotates relative to the rear segment in an X direction, and a plurality of Y direction joint units in which the front segment rotates relative to the rear segment in a Y direction perpendicular to the X direction.

According to an embodiment, the plurality of X direction joint units and the plurality of Y direction joint units may be arranged in an alternating manner along the lengthwise direction.

According to an embodiment, the rotation portion may include a rotation protrusion that is formed on a rear surface of the front segment and has a rotation surface that forms part of a cylinder, and a rotation seat that is formed on a front surface of the rear segment and supports the rotation protrusion.

According to an embodiment, the elastic member may be a plate spring that bends by the pressing force of the front segment.

According to an embodiment, the rear segment may have a central groove that is recessed in the front surface, the rotation seat may be formed in the central groove, and the plate spring may include a connecting portion that is inserted into the central groove, and an elastic portion that is connected to the connecting portion and extends obliquely toward the rear surface of the front segment outside of the central groove.

According to an embodiment, in an initial state in which the joint unit is placed in a straight line, the elastic portion in an unbent state may come into contact with the rear surface of the front segment.

According to an embodiment, the articulating structure may include a plurality of wires that passes through the front segment and the rear segment in the lengthwise direction of the joint unit, the front segment may rotate relative to the rear segment in one direction when a first wire is pulled rearward, the front segment may rotate relative to the rear segment in the other direction opposite the one direction when a second wire in symmetry with the first wire with respect to a lengthwise central axis of the joint unit is pulled rearward, and the plate spring may include a first elastic portion formed on the one direction side and a second elastic portion formed on the other direction side.

According to an embodiment, the connecting portion may be inserted between the rotation protrusion and the rotation seat.

According to an embodiment, the connecting portion may include a curved portion that forms a curve forming part of a cylinder and is inserted between the rotation protrusion and the rotation seat, and a bent portion that is inserted between two rotation seats.

According to an embodiment, the elastic portion may have a notch cut to allow the wire to pass therethrough.

According to an embodiment, the elastic member may be a disc that is inserted into a gap between the front segment and the rear segment, and the disc may be compressed by a pressing force by the rotation of the front segment to provide a force that resists the pressing force.

According to an embodiment, the front segment may rotate relative to the rear segment in the one direction and the other direction opposite the one direction, the elastic member may include a first elastic member that is inserted into the one direction side and a second elastic member that is inserted into the other direction side, the first elastic member and the second elastic member may be inserted into the gap between the front segment and the rear segment while being in a compressed state, and when the front segment rotates in one direction, the first elastic member may be further compressed and resist the rotation of the front segment, and the second elastic member may expand by a restoring force to help the front segment to rotate.

According to another aspect of the present disclosure, there is provided a tube inserting device including an elongated tube, and the articulating structure connected to a front end of the tube.

DETAILED DESCRIPTION

Hereinafter, exemplary embodiments of the present disclosure will be described with reference to the accompanying drawings. The present disclosure is described with reference to the embodiments shown in the drawings, but this is described as one embodiment, and the technical spirit of the present disclosure and its essential elements and operation are not limited thereto.

Figure 1:
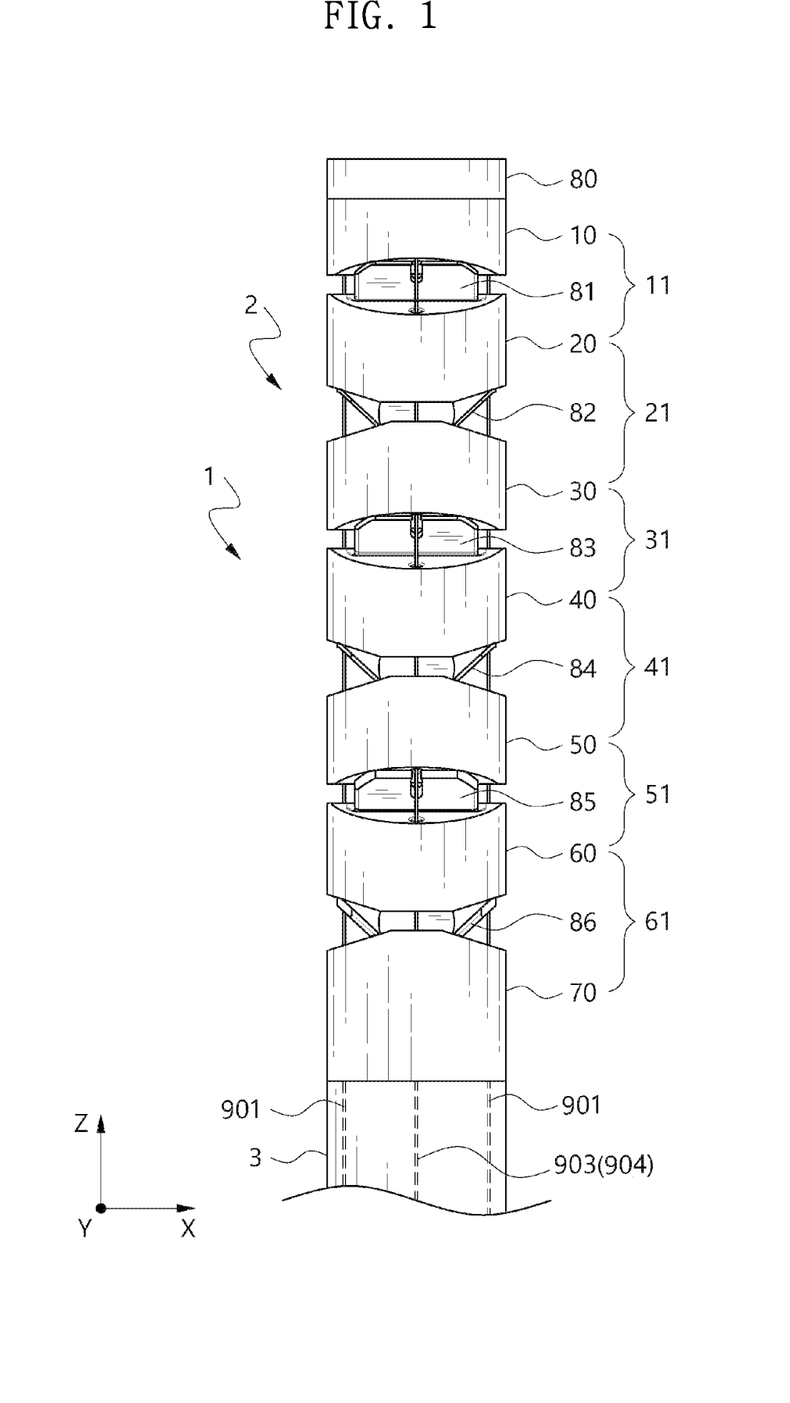
FIG. 1 is a side view of an articulating structure according to an embodiment of the present disclosure and a tube inserting device having the same.

FIG. 1 is a side view of a tube inserting device 1 according to an embodiment of the present disclosure.

For example, the tube inserting device 1 is a microsurgical instrument that is inserted into the body to perform various types of surgeries, and includes a tube 3 that extends longitudinally to be inserted into the body, and an articulating structure 2 according to an embodiment of the present disclosure is attached to the front end of the tube 3.

However, the tube inserting device 1 according to this embodiment is not limited to a microsurgical instrument, and may be used in various types of tasks requiring a tube that is so thin and long as to be inserted into a narrow orifice. Additionally, the articulating structure 2 according to this embodiment is not limited to only the use as an end effector of the tube inserting device 1.

The articulating structure 2 makes bending movements at the front end of the tube 3 to allow stable steering of the tip of the tube inserting device 1 in all directions with high curvature, thereby enhancing the stability and convenience of the non-invasive surgery.

As shown in FIG. 1, the articulating structure 2 includes a plurality of segments 10, 20, 30, 40, 50, 60, 70 connected in series. The articulating structure 2 has a structure such that it is steered by the bending by relative movements of the plurality of segments 10, 20, 30, 40, 50, 60, 70.

In this embodiment, "front" indicates a distal direction of the articulating structure 2, and "rear" indicates a proximal direction of the articulating structure 2. When the articulating structure 2 is placed in a straight line, the front-rear direction of each segment matches the lengthwise direction Z of the articulating structure 2. However, "front" and "rear" are relative terms, and on the contrary, when the distal side of the articulating structure 2 is defined as "rear", the proximal side is defined as "front".

According to this embodiment, a front segment positioned at the front side and a rear segment positioned immediately behind the front segment pair up to form a joint unit.

Accordingly, a first joint unit 11, a second joint unit 21, a third joint unit 31, a fourth joint unit 41, a fifth joint unit 51 and a sixth joint unit 61 are connected in a sequential order from the front side. That is, the articulating structure 2 according to this embodiment includes the plurality of joint units connected in series.

Each joint unit may independently include the front segment and the rear segment, and the rear segment of the front joint unit may be coupled or attached to the front segment of the rear joint unit.

However, according to this embodiment, the rear segment of the front joint unit becomes the front segment of the rear joint unit connected thereto. That is, the connected joint units share one segment as the rear segment of the front joint unit and the front segment of the rear joint unit. Accordingly, it is possible to reduce the total length of the articulating structure 2 and simplify the control operation.

Describing in more detail, as shown in FIG. 1, the first joint unit 11 is formed by a first segment (front segment) 10 and a second segment (rear segment) 20, and the second joint unit 21 is formed by the second segment (front segment) 20 and a third segment (rear segment) 30. The third joint unit 31 is formed by the third segment (front segment) 30 and a fourth segment (rear segment) 40, and the fourth joint unit 41 is formed by the fourth segment (front segment) 40 and a fifth segment (rear segment) 50. The fifth joint unit 51 is formed by the fifth segment (front segment) 50 and a sixth segment (rear segment) 60, and the sixth joint unit 61 is formed by the sixth segment (front segment) 60 and a seventh segment (rear segment) 70.

According to this embodiment, elastic members 81, 82, 83, 84, 85, 86 are interposed between the front segment and the rear segment that form each joint unit.

Hereinafter, referring to FIGS. 2 to 4, the structure of the joint unit will be described in more detail. The description will be provided based on the second joint unit 21.

Figure 2:
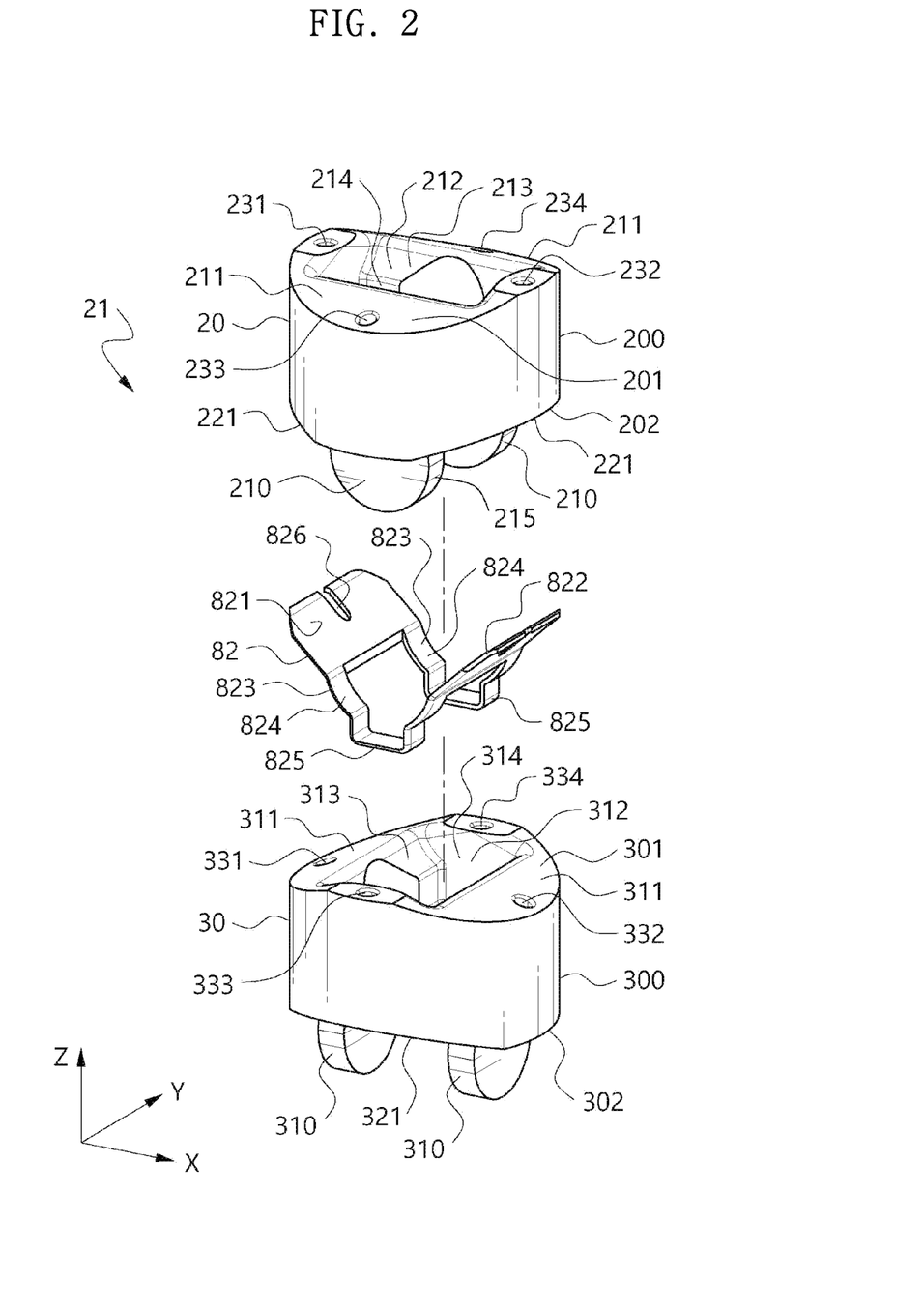
FIG. 2 is an exploded perspective view of a joint unit of the articulating structure of FIG. 1.
Figure 3:
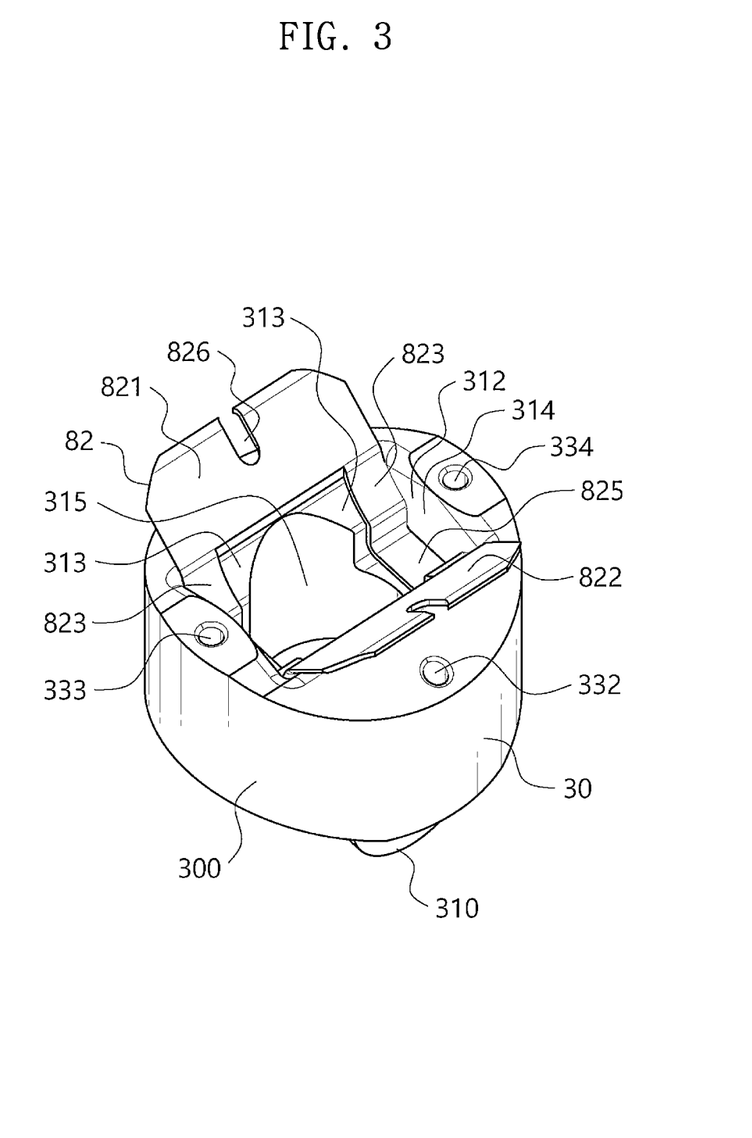
FIG. 3 is a partial perspective view of the joint unit of FIG. 2.
Figure 4:
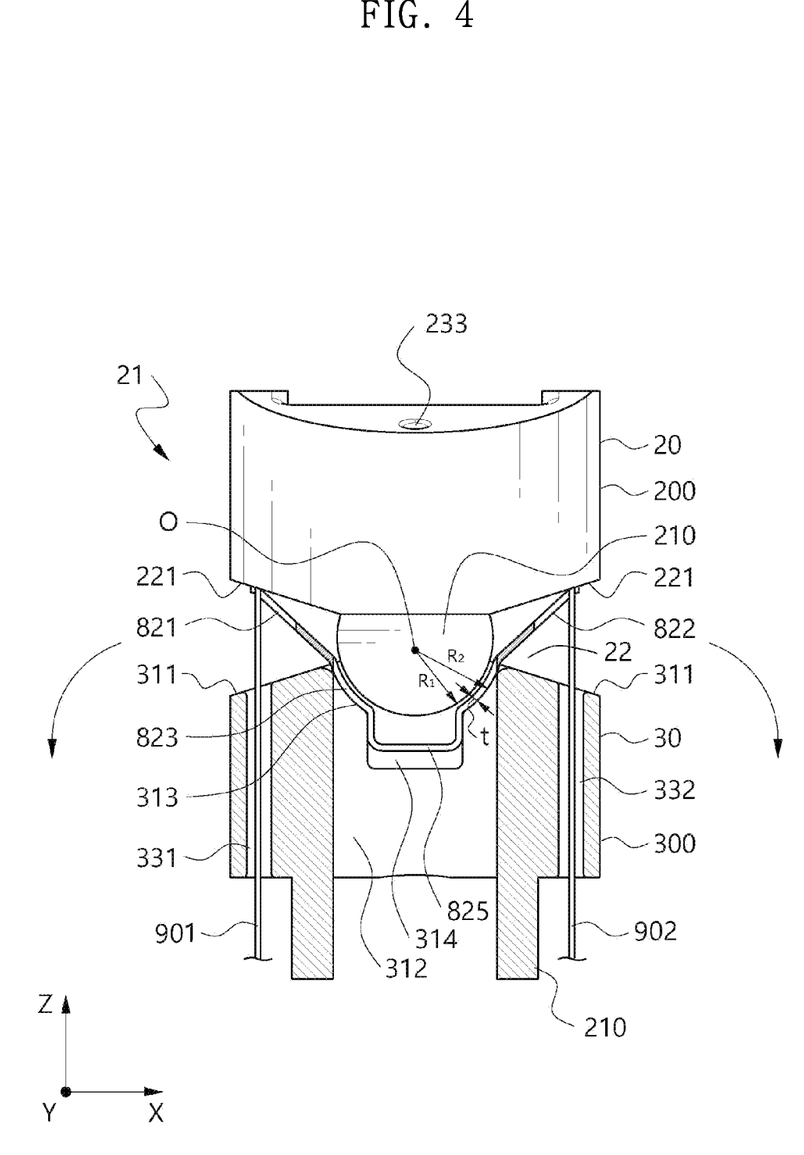
FIG. 4 is a side view of the joint unit of FIG. 2.

FIG. 2 is an exploded perspective view of the second joint unit 21, FIG. 3 is a partial perspective view of the second joint unit 21, and FIG. 4 is a side view of the second joint unit 21. For convenience of description, the rear segment 30 in cross section is shown in FIG. 4.

As shown in FIGS. 2 to 4, the second joint unit 21 includes the front segment 20 and the rear segment 30 connected in series, and the elastic member 82 interposed between the front segment 20 and the rear segment 30.

The front segment 20 includes a body 200 of an approximately cylindrical shape, and two rotation protrusions 210 protruding from a rear surface 202 of the body 200.

The two rotation protrusions 210 are disposed at the center of the front segment 20 when viewed in the Y direction, and spaced apart at a predetermined interval in the Y direction with respect to the lengthwise central axis of the front segment 20.

The rotation protrusion 210 has a cylindrical shape with upper and lower surfaces in the shape of a circle having the radius $R_1$, and a rotation surface 215 between the upper and lower surfaces, the rotation surface 215 forming part of the cylinder.

As best shown in FIG. 4, the rear surface 202 of the front segment 20 includes a sloping portion 221 that is inclined frontward as it goes toward the X direction from the rotation protrusion 210 when viewed in the Y direction.

The rear segment 30 has a body 300 of an approximately cylindrical shape having substantially the same diameter as the front segment 20.

To match with the rear surface 202 of the front segment 20, a front surface 301 of the rear segment 30 includes a sloping portion 311 that is inclined rearward as it goes toward the X direction from the center when viewed in the Y direction.

The sloping portion 221 of the rear surface 202 of the front segment 20 and the sloping portion 311 of the front surface 301 of the rear segment 30 are formed in front-rear symmetry. With the sloping portions 221, 311, it is possible to ensure a high rotation angle with the reduced gap between the front segment 20 and the rear segment 30, thereby reducing the total length of the articulating structure 2.

A central groove 312 recessed rearward from the front surface 301 of the rear segment 30 is formed at the center of the front surface 301.

A central through-hole 315 passing straight through the front and rear sides of the rear segment 30 is formed at the center of the central groove 312. Various types of surgical instruments, for example, an endoscope camera, a lighting device and a surgical instrument, inserted from the rear end of the tube 3 may pass through the joint unit via the central through-hole 315.

Four rotation seats 313 are formed with respect to the central through-hole 315, and a support groove 314 recessed rearward is formed between two rotation seats 313 facing each other in the X direction.

The surfaces of the rotation seats 313 form part of the cylinder having the radius $R_2$ around the central axis O of the rotation protrusion 210 when viewed in the Y direction.

Accordingly, the rotation protrusion 210 may be supported by two rotation seats 313 spaced apart in the X direction. According to this embodiment, the rotation seats 313 support the rotation protrusion 210 with the elastic member 82 interposed between. As the rotation seats 313 supporting the rotation protrusion 210 are formed in the central groove 312 and disposed within the body 300 of the rear segment 30, it is possible to reduce the total length of the second joint unit 21.

A rotation portion 22 for the relative rotation of the front segment 20 and the rear segment 30 is formed by the rotation protrusions 210 of the front segment 20 and the rotation seats 313 of the rear segment 30 where the rotation protrusions 210 are seated.

As shown in FIG. 4, when viewed in the Y direction, the rotation surface 215 of the rotation protrusion 210 and the surfaces of the rotation seats 314 form part of the cylinder around the central axis O of the rotation protrusion 210, and thus the front segment 20 rotates relative to the rear segment 30 rightward and leftward in the X direction around the central axis O of the rotation protrusion 210 as the center of rotation (see the arrow).

In the specification, the joint unit 21 including the front segment 20 rotating relative to the rear segment 30 in the X direction is referred to as an X direction joint unit. In contrast, the joint unit including the front segment rotating relative to the rear segment in the Y direction perpendicular to the X direction is referred to as a Y direction joint unit.

According to this embodiment, the rotation of the front segment 20 and the rear segment 30 is accomplished by wires 901, 902.

As shown in FIG. 2, a first wire connecting hole 231 passing through the front segment 20 from a front surface 201 to the rear surface 202 is formed on one side of the front segment 20. A second wire connecting hole 232 passes through the front and rear sides of the front segment 20 at a location which is symmetric to the first wire connecting hole 231 with respect to the lengthwise central axis (the lengthwise central axis of the joint unit) of the front segment 20. The first wire connecting hole 231 and the second wire connecting hole 232 are spaced apart in the X direction, and the rotation protrusions 210 are disposed in between the first wire connecting hole 231 and the second wire connecting hole 232.

Likewise, the rear segment 30 has a first wire connecting hole 331 and a second wire connecting hole 332 passing through the front and rear sides of the rear segment 30. The first wire connecting hole 331 and the second wire connecting hole 332 are spaced apart in the X direction, and the central groove 312 is disposed in between the first wire connecting hole 331 and the second wire connecting hole 332.

As shown in FIG. 4, a first wire 901 passes through the first wire connecting hole 231 of the front segment 20 and the first wire connecting hole 331 of the rear segment 30, and a second wire 902 passes through the second wire connecting hole 232 of the front segment 20 and the second wire connecting hole 332 of the rear segment 30.

When the first wire 901 is pulled rearward, the front segment 20 rotates relative to the rear segment 30 in one direction (−X direction) around the central axis O of rotation. On the contrary, when the second wire 902 is pulled rearward, the front segment 20 rotates relative to the rear segment 30 in the other direction (+X direction) opposite −X direction around the central axis O of rotation.

The rotation control of the articulating structure by the wire disposed eccentrically from the lengthwise central axis of the joint unit is well known. However, the articulating structure 2 according to this embodiment improves the motion characteristics of the articulating structure 2 with the elastic member interposed between the front segment and the rear segment of the joint unit.

As shown in FIGS. 2 to 4, the elastic member 82 according to this embodiment is a sort of plate spring formed by bending a plate member.

The elastic member 82 includes a connecting portion 823 inserted into the central groove 312 of the rear segment 30, and elastic portions 821, 822 connected to the connecting portion 823 and extending obliquely toward the rear surface 202 (the sloping portion 221) of the front segment 20 outside of the central groove 312.

The elastic member 82 includes two connecting portions 823 spaced apart in the Y direction. As shown in FIG. 3, the two connecting portions 823 are spaced apart, each in contact with the side of the central groove 312, and have a width which does not cover the central through-hole 315.

The connecting portion 823 includes two curved portions 824 arranged in the X direction and a bent portion 825 bent rearward between the two curved portions 824.

The two curved portions 824 form a curve that forms part of the cylinder around the central axis O of the rotation protrusion 210 when viewed in the Y direction. The inner radius of the curved portions 824 is substantially the same as the radius $R_1$ of the rotation protrusion 210, and the outer radius of the curved portions 824 is substantially the same as the radius $R_2$ of the rotation seats 313.

The two curved portions 824 are each placed on the two rotation seats 313 arranged in the X direction, and the rotation protrusion 210 of the front segment 20 is placed thereon. The connecting portions 823 of the elastic member 82 are inserted and fixed between the rotation protrusion 210 and the rotation seats 313.

Since the inner radius of the curved portions 824 is substantially the same as the radius R1 of the rotation protrusion 210 and the outer radius of the curved portions 824 is substantially the same as the radius R2 of the rotation seats 313, the interference of the elastic member 82 does not occur at the rotation portion 22 during the rotational movement of the front segment 20.

The bent portion 825 is bent rearward in the shape of approximately "⊏", and is inserted between the two rotation seats 313 arranged in the X direction, i.e., the support groove 314.

As described above, the connecting portions 823 of the elastic member 82 fit the central groove 312, so the X direction and Y direction location of the elastic member 82 is fixed, and the Z direction (lengthwise direction of the joint unit) location is also firmly fixed when interposed between the front segment 20 and the rear segment 30. Additionally, when the front segment 20 rotates relative to the rear segment 30, the bent portion 825 may prevent the elastic member 82 from being tilted by friction.

The first elastic portion 821 is formed on one direction (−X direction) side of the connecting portion 823, and the second elastic portion 822 is formed on the other direction (+X direction) side. When viewed in the Y direction, the first elastic portion 821 and the second elastic portion 822 are formed in symmetry.

In the initial state (FIG. 4) in which the second joint unit 21 is not bent and is placed in a straight line, the first elastic portion 821 and the second elastic portion 822 do not bend and come in contact with the sloping portion 221 of the rear surface 202 of the front segment 20. That is, as shown in FIG. 4, the ends of the first elastic portion 821 and the second elastic portion 822 support the front segment 20 symmetrically in the X direction.

A notch 826 is cut at the center of the first elastic portion 821 and the second elastic portion 822 to allow the wire to pass therethrough. By forming the notches 826, the ends of the first elastic portion 821 and the second elastic portion 822 that contact the front segment 20 may be placed on the outer side of the front segment 20, thereby reducing the burden of resistance of the elastic member 82 during rotation.

When the front segment 20 rotates, for example, in one direction (−X direction) in the initial state in which the front segment 20 and the rear segment 30 are arranged in a straight line, the rear surface 202 of the front segment 20 presses down the first elastic portion 821.

The connecting portion 823 of the elastic member 82 is fixed between the front segment 20 and the rear segment 30, and the first elastic portion 821 is pressed and bent by the pressing force by the rotation of the front segment 20. Accordingly, the first elastic portion 821 elastically deforms to provide an elastic force that resists the pressing force of the front segment 20.

The elastic force provided by the first elastic portion 821 and the pressing force are kept balanced during the action of the pressing force by the rotation of the front segment 20, and the first elastic portion 821 supports the rear side of the front segment 20 by the force that resists the pressing force. Accordingly, it is possible to prevent the sudden rotation of the front segment 20, so-called "buckling" when the load applied to the front segment 20 reaches a certain magnitude.

Accordingly, it is possible to perform the rotational movement of the front segment 20 more accurately and stably.

Additionally, when restoring (stretching) the front segment 20 (bent) rotated relative to the rear segment 30 to the original position, a larger force is generally required to stretch the front segment 20 bent relative to the rear segment 30 than a force required to bend due to the load of the front segment 20. According to this embodiment, the elastic force of the first elastic portion 821 stored during the rotation of the front segment 20 pushes the front segment 20 when the front segment 20 is stretched, and accordingly it is possible to stretch the front segment 20 with a smaller force.

Further, when the front segment 20 is stretched by rotation in the opposite direction to the original rotation direction and the front segment 20 and the rear segment 30 are aligned in a straight line into the initial state, the second elastic portion 822 comes into contact with the front segment 20 to prevent the front segment 20 from rotating any longer, and accordingly it is possible to easily align the front segment 20 and the rear segment 30 in a linear state (initial state).

While the second joint unit 21 which is the X direction joint unit rotating in the X direction has been hereinabove described, the articulating structure 2 according to this embodiment may be steered in 3-dimensions in combination with the Y direction joint unit rotating in the Y direction perpendicular to the X direction.

Referring to FIG. 2, in the similar way to the rear segment 30, the front segment 20 has a sloping portion 211 and a central groove 212 on the front surface 201. There is a difference between the front segment 20 and the rear segment 30 in that two sloping portions 211 of the front segment 20 are inclined rearward as it goes toward the Y direction from the center when viewed in the X direction. That is, the sloping portions 211 of the front surface 201 of the front segment 20 correspond to 90° rotation of the sloping portions 311 of the front surface 301 of the rear segment 30 (also correspond to 90° rotation of the sloping portions 221 of the rear surface 202).

Additionally, the central groove 212 of the front segment 20 has the same configuration as the central groove 312 of the rear segment 30, but the central groove 212 of the front segment 20 and the central groove 312 of the rear segment 30 are positioned by 90°. That is, when viewed in the X direction, the surfaces of rotation seats 213 form part of the cylinder around an axis parallel to the X axis as the central axis, and a support groove 214 is formed between two rotation seats 213 spaced apart in the Y direction.

In addition to the first and second wire connecting holes 231, 232, the front segment 20 has a third wire connecting hole 233 and a fourth wire connecting hole 234 spaced apart in the Y direction, and the third wire connecting hole 233 and the fourth wire connecting hole 234 pass through the front and rear sides of the front segment 20. The two rotation protrusions 210 are disposed in between the third wire connecting hole 233 and the fourth wire connecting hole 234.

The rear segment 30 includes two rotation protrusions 310 protruding from a rear surface 302. The two rotation protrusions 310 are disposed at the center of the rear segment 30 when viewed in the X direction, and spaced apart at a predetermined interval in the X direction with respect to the lengthwise central axis of the rear segment 30.

The rear surface 302 of the rear segment 30 includes a sloping portion 321 that is inclined frontward as it goes toward the Y direction from the rotation protrusion 310 when viewed in the X direction.

Additionally, in addition to the first and second wire connecting holes 331, 332, the rear segment 30 has a third wire connecting hole 333 and a fourth wire connecting hole 334 spaced apart in the Y direction, and the third wire connecting hole 333 and the fourth wire connecting hole 334 pass through the front and rear sides of the rear segment 30. The two rotation protrusions 310 are disposed in between the third wire connecting hole 333 and the fourth wire connecting hole 334.

In other words, according to this embodiment, the front segment 20 and the rear segment 30 have substantially the same structure, but they are oriented by 90° with respect to the Z direction.

According to this embodiment, the segments having substantially the same structure are connected by 90° with respect to the Z direction to form the articulating structure 2 including the X direction joint unit and the Y direction joint unit in combination.

In FIG. 2, when the X axis and the Y axis are rotated 90° by rotating the left bottom coordinate axis around the Z axis, the reference numbers 20 and 30 are replaced with 10 and 20 respectively and the reference numbers 200s and 300s are replaced with 100s and 200s respectively, the joint unit 21 will be the first joint unit 11 formed by the first segment (front segment) 10 and the second segment (rear segment) 20. In this instance, the elastic member 82 will be the elastic member 81.

Additionally, in FIG. 2, when X axis and the Y axis are rotated 90° by rotating the left bottom coordinate axis around the Z axis, the reference numbers 20 and 30 are replaced with 30 and 40 respectively and the reference numbers 200s and 300s are replaced with 300s and 400s respectively, the joint unit 21 will be the third joint unit 31 formed by the third segment (front segment) 30 and the fourth segment (rear segment) 40. In this instance, the elastic member 82 will be the elastic member 83.

Additionally, in FIG. 2, when X axis and the Y axis are rotated 90° by rotating the left bottom coordinate axis around the Z axis, the reference numbers 20 and 30 are replaced with 50 and 60 respectively and the reference numbers 200s and 300s are replaced with 500s and 600s, the joint unit 21 will be the fifth joint unit 51 formed by the fifth segment (front segment) 50 and the sixth segment (rear segment) 60. In this instance, the elastic member 82 will be the elastic member 85.

The first joint unit 11, the third joint unit 31 and the fifth joint unit 51 are all Y direction joint units including the front segment rotating relative to the rear segment in the Y direction.

Referring back to FIG. 1, the rotation of the Y direction joint units 11, 31, 51 in the Y direction is performed by a third wire 903 passing through the third wire connecting hole and a fourth wire 904 passing through the fourth wire connecting hole.

On the other hand, in FIG. 2, when the left bottom coordinate axis remains as it is, the reference numbers 20 and 30 are replaced with 40 and 50 respectively and the reference numbers 200s and 300s are replaced with 400s and 500s respectively, the joint unit 21 will be the fourth joint unit 41 formed by the fourth segment (front segment) 40 and the fifth segment (rear segment) 50. In this instance, the elastic member 82 will be the elastic member 84.

Additionally, in FIG. 2, when the left bottom coordinate axis remains as it is, the reference numbers 20 and 30 are replaced with 60 and 70 respectively and the reference numbers 200s and 300s are replaced with 600s and 700s respectively, the joint unit 21 will be the sixth joint unit 61 formed by the sixth segment (front segment) 60 and the seventh segment (rear segment) 70. In this instance, the elastic member 82 will be the elastic member 86. Here, in this embodiment, as opposed to the other segments, the seventh segment 70 disposed at the rearmost side does not have the rotation protrusions and the sloping portions, and has a flat rear surface for easy coupling with the tube 3. However, the present disclosure is not limited thereto, and similar to a cap 80 that covers the front side of the first segment 10 positioned at the frontmost side, the rear side of the seventh segment 70 having the same configuration as the third segment 30 may be covered with a cap to form a flat rear surface.

The second joint unit 21, the fourth joint unit 41 and the sixth joint unit 61 are all X direction joint units including the front segment rotating relative to the rear segment in the X direction.

Referring back to FIG. 1, the rotation of the X direction joint units 21, 41, 61 in the X direction is performed by the first wire 901 passing through the first wire connecting hole and the second wire 902 passing through the second wire connecting hole.

When the segments having the same structure are connected in series by 90°, the articulating structure 2 is formed with the plurality of X direction joint units 21, 41, 61 and the plurality of Y direction joint units 11, 31, 51 arranged in an alternating manner along the lengthwise direction.

The front ends of the four wires 901, 902, 903, 904 are fixed to the cap 80 disposed at the front side of the first segment 10. The rear ends of the wires 901, 902, 903, 904 extend to the rear end of the tube 3 via the inside of the tube 3 throughout the articulating structure 2. A wire driving means not shown is installed at the rear end of the tube 3, and the wires 901, 902, 903, 904 are connected to the wire driving means. The wire driving means operates to pull or release each of the wires 901, 902, 903, 904 in the lengthwise direction Z of the articulating structure 2.

The wires 901, 902, 903, 904 are formed from a material having slight elasticity, and in the initial state, the wire driving means tightly pulls the wires 901, 902, 903, 904 with the same tension. Accordingly, a force is applied rearward to the articulating structure 2 symmetrically in the X direction and Y direction. The articulating structure 2 may be fixed in linearly stretched state (initial state) by the balanced tension of the wires on opposing sides.

To steer the articulating structure 2, for example, the wire driving means may pull the first wire 901 to increase the tension, and on the other hand, may release the tension applied to the second wire 902.

Accordingly, the left direction of X direction of the first segment 10 is pulled rearward by the cap 80, and the cap 80 presses the first to sixth segments rearward.

In this instance, the front segments and the rear segments of the Y direction joint units 11, 31, 51 having the central axis of rotation in the X axis direction cannot make relative movements. In contrast, the front segments and the rear segments of the X direction joint units 21, 41, 61 having the central axis of rotation in the Y axis direction are tilted in one direction (−X direction) (see FIG. 6).

Figure 6:
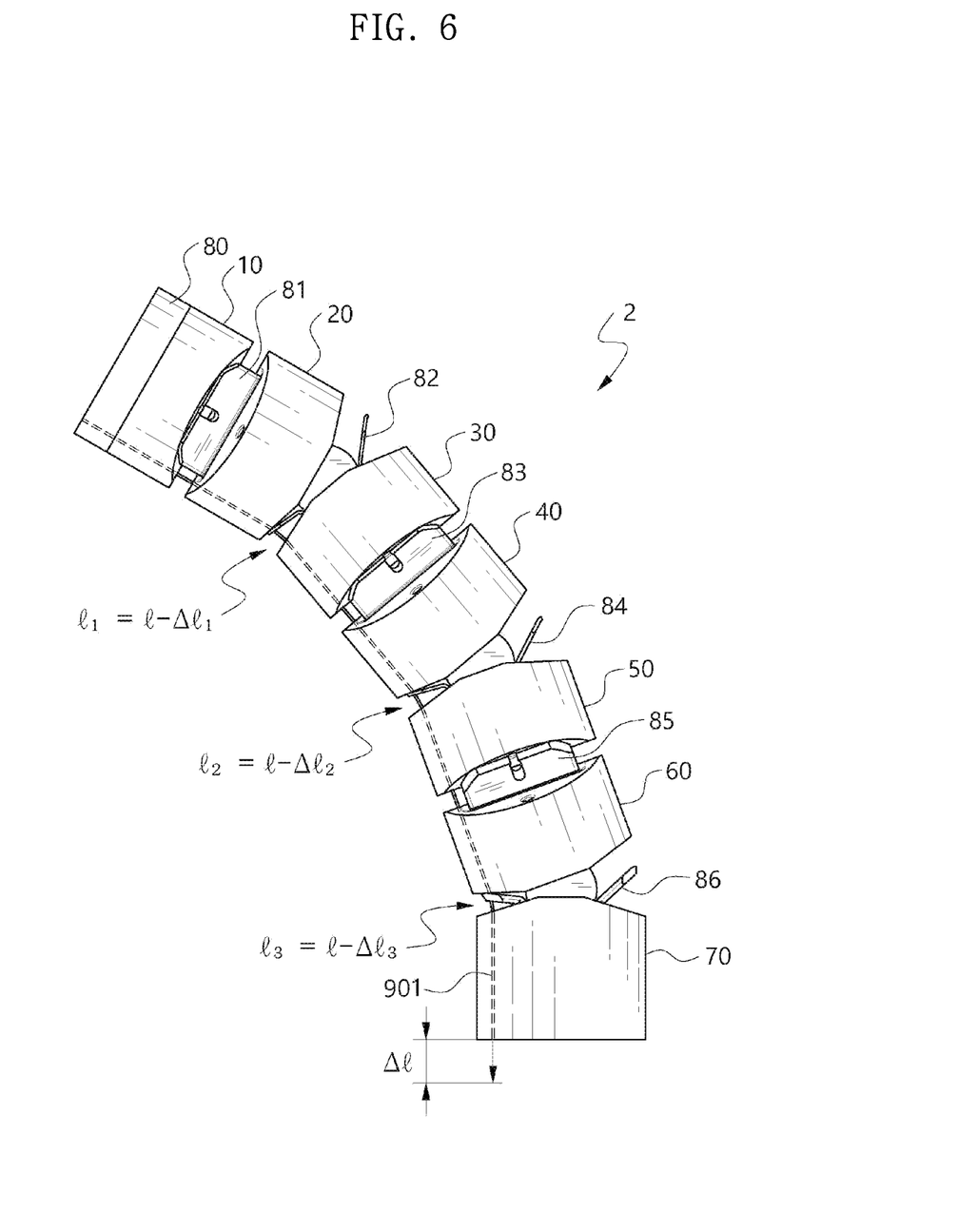
FIGS. 6 and 7 are diagrams showing the bent state of an articulating structure with varying elastic coefficients of an elastic member of each joint unit.

That is, when the relative positions of the front segments and the rear segments of the Y direction joint units 11, 31, 51 are fixed, and in this state, the front segments of the X direction joint units 21, 41, 61 are each bent relative to the rear segments, the entire articulating structure 2 is steered in one direction (leftward direction in FIG. 6).

In this instance, as described above, buckling does not occur by the action of the elastic member of each joint unit, and the entire articulating structure 2 is softly steered.

When the wire driving means pulls the second wire 902 to increase the tension while releasing the tension applied to the first wire 901, the front segments of the X direction joint units 21, 41, 61 rotate relative to the rear segments in the other direction (X direction), and the articulating structure 2 steered in one direction may restore to the initial state. In this instance, as described above, it is possible to easily restore to the initial state with a smaller force by the action of the elastic member.

Further, when the wire driving means keeps pulling the second wire 902 while releasing the tension applied to the first wire 901, the articulating structure 10 may be steered in the other direction (rightward direction in FIG. 6) contrary to FIG. 6.

Likewise, it will be understood that when the third wire 903 and the fourth wire 904 are pulled or released by the wire driving means, the front segments and the rear segments of the X direction joint units 21, 41, 61 cannot make relative movements, while the front segments and the rear segments of the Y direction joint units 11, 31, 51 are tilted in the two directions of the Y direction.

Although X direction steering and Y direction steering of the articulating structure 2 are separately described above, it will be understood that the first to fourth wires 901, 902, 903, 904 may be manipulated by the wire driving means at the same time for simultaneous X direction steering and Y direction steering of the articulating structure 2. That is, the tip of the articulating structure 2 may be steered in 3-dimensions within the range of bend limit of the articulating structure 2.

The X direction steering and Y direction steering of the articulating structure 2 are independently accomplished by the pair of wires arranged in the X direction and the pair of wires arranged in the Y direction, respectively, resulting in relatively simple computation for 3-dimensional composite direction control of the tip.

Although this embodiment shows that the X direction joint unit and the Y direction joint unit are arranged in an alternating manner along the lengthwise direction, the present disclosure is not limited thereto.

For example, when a segment (a non-alternating segment) including two rotation protrusions 310 arranged in the Y direction and two sloping portions 321 of the rear surface 302 arranged in the X direction is connected in series to the third segment 30 (an alternating segment), the articulating structure may bend only in the X direction. Additionally, when the alternating segment and the non-alternating segment are appropriately combined, the X direction joint unit and the Y direction joint unit may be arranged in many other combinations.

Additionally, according to this embodiment, assembling is enhanced since the rotation portion is formed through the rotation protrusions and the rotation seats, but the present disclosure is not limited thereto. When the elastic member is fixed to the rear segment (or the front segment), the rotation portion may be formed, for example, by pin coupling.

Although the above-described embodiment describes that the same elastic member may be used, the articulating structure may include a combination of elastic members having same or different elastic coefficients.

Referring to FIG. 4, the elastic member 82 according to this embodiment is a plate spring having whole uniform thickness. The elastic coefficient of the plate spring type elastic member may be adjusted by changing the thickness of the plate spring.

According to this embodiment, the thickness t of the plate spring is approximately $R_2-R_1$. With the increasing/decreasing outer radius $R_2$ of the curved portion 824 of the elastic member 82 while keeping the inner radius $R_1$ uniform, the thickness of the elastic member increases/decreases, and the elastic coefficient increases/decreases accordingly. In response to the increasing/decreasing outer radius $R_2$ of the curved portion 824, the rear segment 30 has a change in the size of an arc of the rotation seat 313 of the rear segment 30, i.e., the radius $R_2$.

Figure 5:
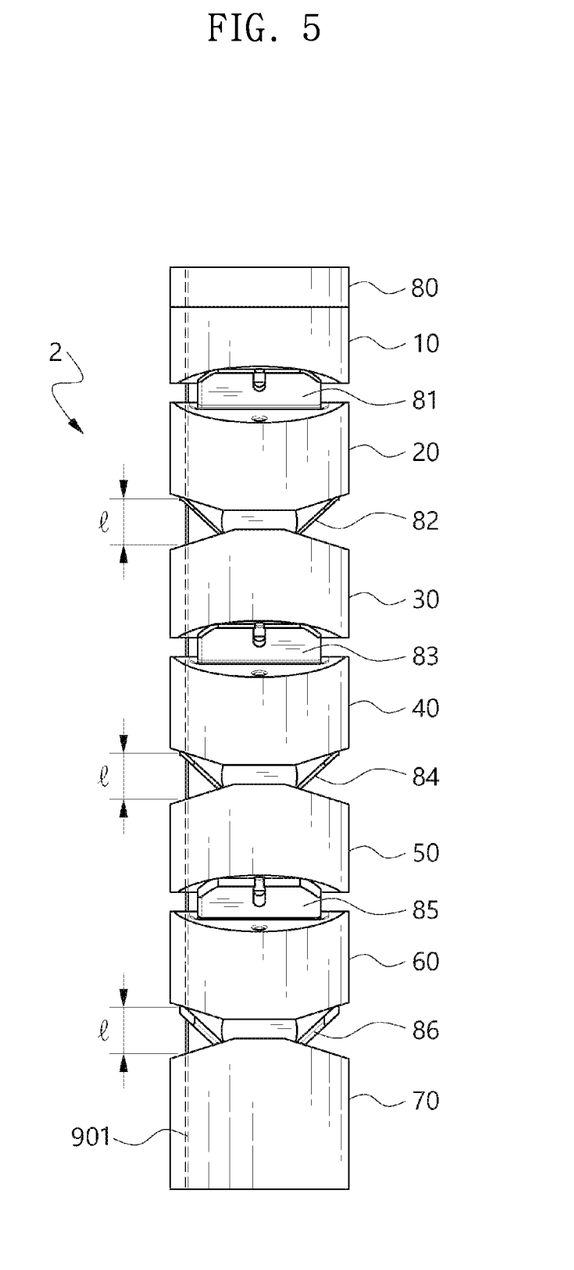
FIG. 5 is a diagram showing an articulating structure in initial state.
Figure 7:
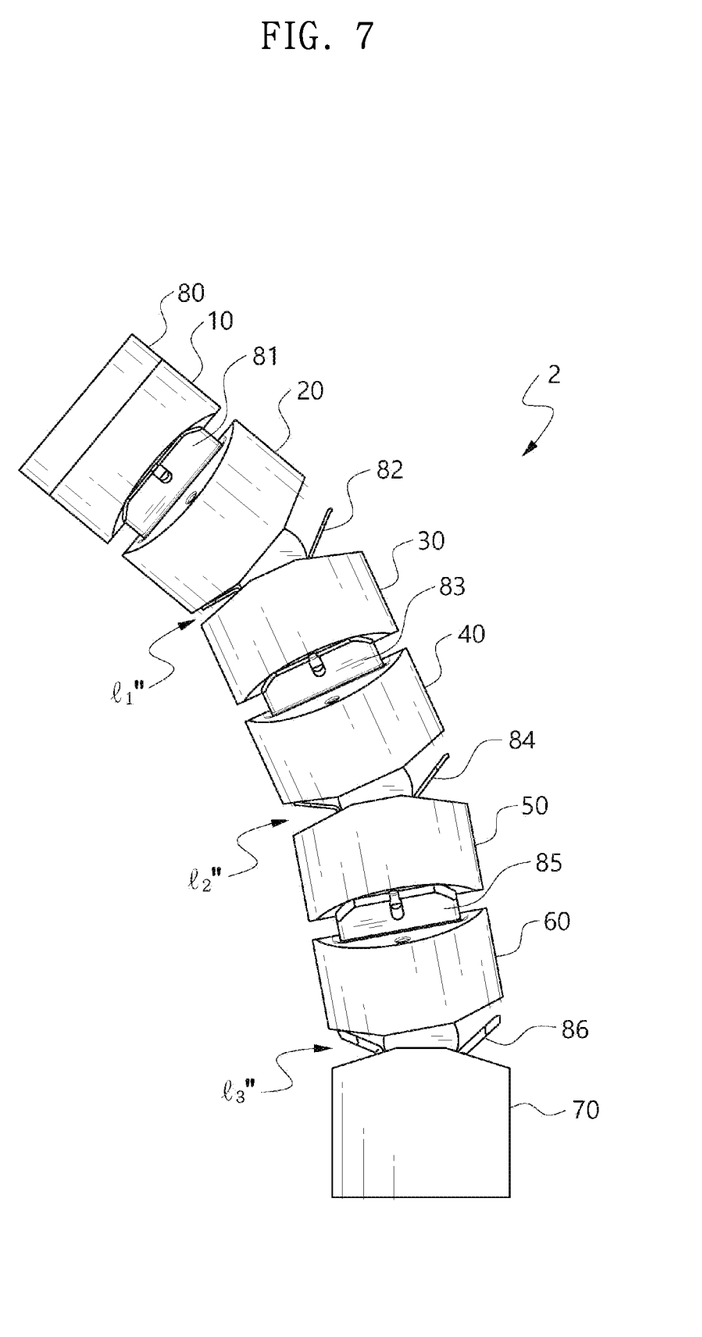

FIGS. 5 to 7 are diagrams illustrating the bent state of the articulating structure 2 according to the elastic coefficient of the elastic member of each of the X direction joint units 21, 41, 61.

The elastic coefficient of the elastic member 82 of the second joint unit 21 is the elastic coefficient of the elastic member 84 of the fourth joint unit 41 is $k_2$, and the elastic coefficient of the elastic member 86 of the sixth joint unit 61 is $k_3$. Additionally, as shown in FIG. 5, the length of the first wire 901 exposed between the front segment and the rear segment of each of the X direction joint units 21, 41, 61 in the initial state of the articulating structure 2 placed in linear state is l.

When the articulating structure 2 is bent in one direction (-X direction) by pulling the first wire 901 by Δl, the length $l_1$ of the wire exposed between the front segment and the rear segment of the second joint unit 21 is $l-\Delta l_1$, the length $l_2$ of the wire exposed between the front segment and the rear segment of the fourth joint unit 41 is $l-\Delta l_2$, and the length $l_3$ of the wire exposed between the front segment and the rear segment of the sixth joint unit 61 is $l-\Delta l_3$ ($\Delta l=\Delta l_1+\Delta l_2+\Delta l_3$).

FIG. 6 is a diagram showing the bent state of the articulating structure 2 when $k_1$ is 0.15 N/mm, $k_2$ is 0.10 N/mm, and $k_3$ is 0.05 N/mm (i.e., $k_1>k_2>k_3$). In this case, a ratio of $l_1(l-\Delta l_1)$, $l_2(l-\Delta l_2)$ and $l_3(l-\Delta l_3)$ is 1.0552:0.8734:0.3279. That is, it can be seen that the bending angle ascends in the order of the sixth joint unit 61, the fourth joint unit 41 and the second joint unit 21.

FIG. 7 is a diagram showing the bent state of the articulating structure 2 when $k_1$ is 0.05 N/mm, $k_2$ is 0.10 N/mm, and $k_3$ is 0.15 N/mm (i.e., $k_3>k_2>k_1$). In this case, a ratio of $l_1(l-\Delta l_1)$, $l_2(l-\Delta l_2)$ and $l_3(l-\Delta l_3)$ is 0.3279:0.8734:1.0552. That is, it can be seen that the bending angle ascends in the order of the second joint unit 21, the fourth joint unit 41 and the sixth joint unit 61.

It can be seen that even though the first wire 901 is pulled by the same length Δl, the bending of the articulating structure 2 changes depending on the elastic coefficients of the elastic members. In the case of FIG. 6, the entire articulating structure 2 is bent at a higher bending angle than that of FIG. 7.

Although not shown, when $k_1$ is 0.10 N/mm, $k_2$ is 0.05 N/mm and $k_3$ is 0.15 N/mm (i.e., $k_1>k_3>k_2$), a ratio of $l_1$, $l_2$ and $l_3$ is 0.8734:0.3279:1.0552 and the bending angle of the fourth joint unit 41 is highest. Accordingly, even though the first wire 901 is pulled by the same length Δl, the bending angle of the entire articulating structure 2 will be intermediate between FIGS. 6 and 7.

This is because when the articulating structure 2 is bent in one direction (-X direction) by pulling the first wire 901, the angle of the joint is formed toward a lower total energy sum, the total energy sum obtained by summing up the values of elastic energy generated by the pressed elastic members 82, 84, 86.

In more detail, Equation for finding the sum of elastic energy is, for example, the following [Equation].

$$\text{sum}(E)=\sum_{i=1}^{n} \tfrac{1}{2} k_i \Delta l_i^2 \quad \text{[Equation]}$$

(where n=3)

Each length $\Delta l_1$, $\Delta l_2$, $\Delta l_3$ at which the sum of energy is minimum may be calculated from the above [Equation].

Since it is possible to calculate each length $\Delta l_1$, $\Delta l_2$, $\Delta l_3$ at which the sum of energy is minimum, even though the wire is pulled by the same length, it is possible to adjust the bending angle of each joint unit by adjusting the elastic coefficient of the elastic member of the joint unit.

Further, as the second joint unit 21, the fourth joint unit 41 and the sixth joint unit 61 are bent in a sequential order from the joint unit having a weaker support force provided by the elastic member, it is possible to estimate the bending order of the joint units.

Compared to the conventional art in which the bending angle and the bending order of the joint units are uniform in response to the length of the wire being pulled, according to this embodiment, the bending angle or the bending order of the entire articulating structure may be determined according to the working environment or condition. Accordingly, it is possible to select the type of bending of the articulating structure by adaptively responding to the type of working environment in which the articulating structure is used.

Although only the X direction joint units are described above by way of illustration and the elastic coefficient of the elastic member of each of the X direction joint units is different, the present disclosure is not limited thereto. The elastic coefficients of the elastic members of all the joint units of the articulating structure 2 including the Y direction joint units may be the same or different in whole or in part. That is, the elastic coefficients of some joint units may be the same, and the elastic coefficients of some joint units may be different. Additionally, one X direction joint unit and one Y direction joint unit connected thereto may pair up, and the elastic coefficients of one pair of joint units may be the same, and the elastic coefficients of the other pair of joint units may be different.

By setting various combinations of elastic coefficients, it is possible to selectively form the articulating structure that bends in various shapes according to the working environment or condition.

According to this embodiment, the elastic member is shown as a sort of plate spring by way of illustration, but is not limited thereto.

Figure 8:
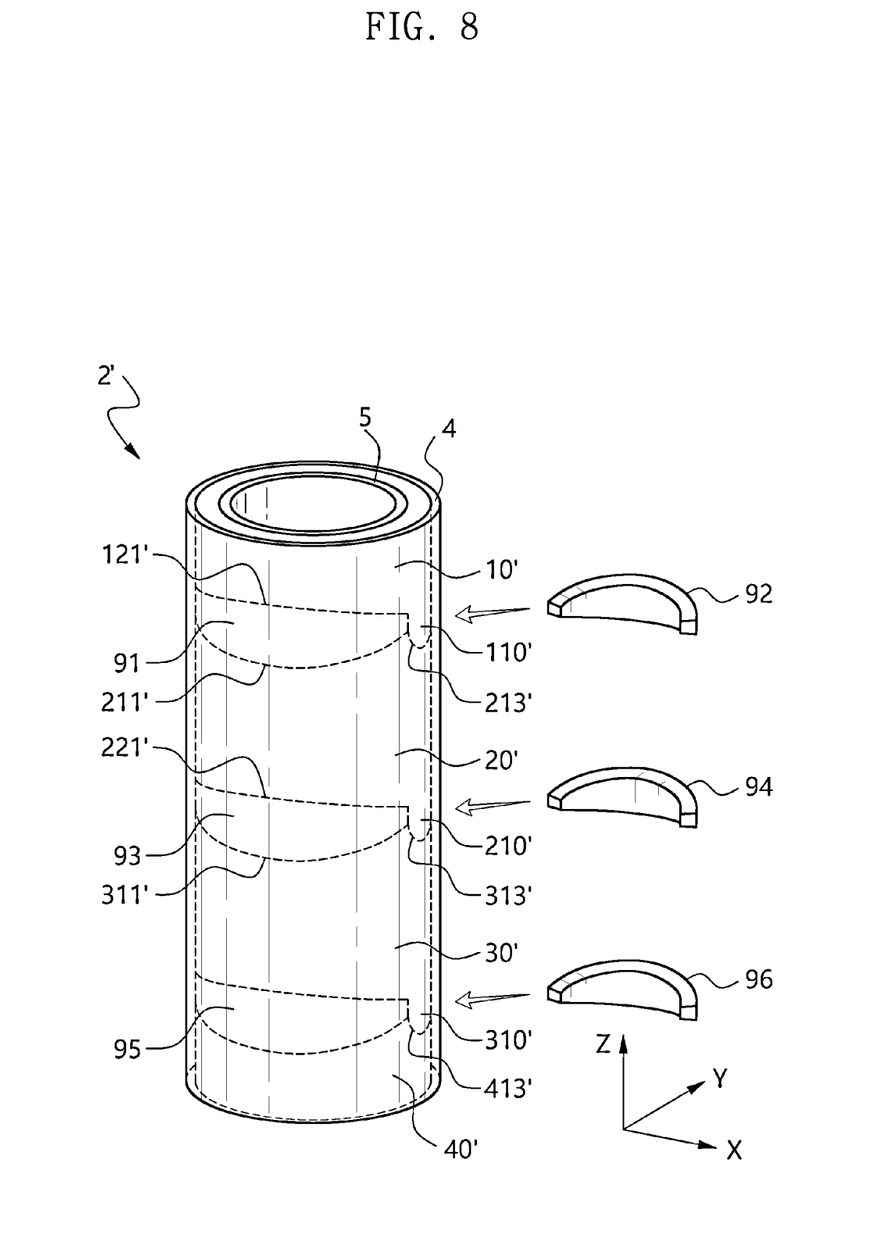
FIG. 8 is a schematic perspective view of an articulating structure according to another embodiment of the present disclosure.

FIG. 8 is a schematic perspective view of an articulating structure 2' according to another embodiment of the present disclosure.

The articulating structure 2' according to this embodiment has a single direction rotation structure in the Y direction, but is not limited thereto.

A first segment 10' includes two rotation protrusions 110' protruding from a rear surface and arranged in the X direction, and a sloping portion 121' formed obliquely frontward from the rotation protrusions 110'.

A second segment 20' has rotation grooves 213' recessed on a front surface to support the rotation protrusions 110'. The rotation protrusions 110' of the front segment 10' and the rotation grooves 213' of the rear segment 20' form a rotation portion.

A sloping portion 211' formed obliquely rearward from the rotation grooves 213' is formed on the front surface of the second segment 20'.

A first elastic member 91 and a second elastic member 92 are each inserted into a nail shaped gap between the first segment 10' and the second segment 20' formed by the sloping portion 121' and the sloping portion 211'.

The first elastic member 91 and the second elastic member 92 are disc shaped members that are made of polymer and can be compressed, and conform to the shape of the nail shaped gap between the first segment 10' and the second segment 20' to completely fill the gap between the first segment 10' and the second segment 20'. According to this configuration, the elastic member may apply a uniform force over the entire periphery of the gap between the first segment 10' and the second segment 20'.

The outer side and the inner side of the first segment 10' and the second segment 20' are covered with a flexible outer covering 4 and a flexible inner covering 5 over the entire length of the articulating structure 2' to prevent slips of the elastic members 91, 92.

The first segment (front segment) 10', the second segment (rear segment) 20' and the elastic members 91, 92 interposed between form a first joint unit.

Two wires (not shown) arranged in the Y direction are connected such that they pass through the first segment (front segment) 10' and the second segment (rear segment) 20' in the lengthwise direction. In this instance, each wire may pass through the elastic members 91, 92 in the lengthwise direction.

When the first segment 10' rotates relative to the second segment 20' in one direction (−Y direction) by pulling the first wire (not shown), the first elastic member 91 is pressed by the sloping portion 121' of the first segment 10', then compressed by the pressing force, and provides a force that resists the pressing force. The operation of the first elastic member 91, 92 of disc shape is substantially the same as the elastic member 82 of the previous embodiment.

However, according to this embodiment, the first elastic member 91 and the second elastic member 92 are not necessarily formed with the same size as the gap between the first segment 10' and the second segment 20' aligned in a straight line. The first elastic member 91 and the second elastic member 92 may be formed with a slightly larger size than the gap between the first segment 10' and the second segment 20', and may be inserted in slightly compressed state between the first segment 10' and the second segment 20'.

Accordingly, when the front segment 10' rotates relative to the rear segment 20' in one direction (−Y direction), the first elastic member 91 inserted in one direction is further compressed and resists the rotation of the front segment 10', while the second elastic member 92 inserted in the other direction (+Y direction) expands by a restoring force and pushes the front segment 10' to help the front segment 10' to rotate. When the front segment 10' rotates relative to the rear segment 20' in the other direction (+Y direction) by pulling the second wire (not shown), the first elastic member 91 expands and the second elastic member 92 is compressed.

According to this configuration, the expansion force of the elastic member is added to the tension of the wire, making it possible to rotate the front segment with a smaller force.

The second segment 20' includes two rotation protrusions 210' protruding from a rear surface and arranged in the X direction, and a sloping portion 221' formed obliquely frontward from the rotation protrusions 210'.

A third segment 30' has rotation grooves 313' recessed on a front surface to support the rotation protrusions 210'. The rotation protrusions 210' of the front segment 20' and the rotation grooves 313' of the rear segment 30' form a rotation portion.

A sloping portion 311' formed obliquely rearward from the rotation grooves 313' is formed on the front surface of the third segment 30'.

A third elastic member 93 and a fourth elastic member 94 are each inserted into a nail shaped gap between the second segment 20' and the third segment 30' formed by the sloping portion 221' and the sloping portion 311'.

The second segment (front segment) 20', the third segment (rear segment) 30' and the elastic members 93, 94 interposed between form a second joint unit.

The third segment 30' includes two rotation protrusions 310' protruding from a rear surface and arranged in the X direction, and a sloping portion 321' formed obliquely frontward from the rotation protrusions 310'.

A fourth segment 40' has rotation grooves 413' recessed on a front surface to support the rotation protrusions 310'. The rotation protrusions 310' of the front segment 30' and the rotation grooves 413' of the rear segment 40' form a rotation portion.

A sloping portion 411' formed obliquely rearward from the rotation grooves 413' is formed on the front surface of the fourth segment 30'.

A fifth elastic member 95 and a sixth elastic member 96 are each inserted into a nail shaped gap between the third segment 30' and the fourth segment 40' formed by the sloping portion 321' and the sloping portion 411'.

The third segment (front segment) 30', the fourth segment (rear segment) 40' and the elastic members 95, 96 interposed between form a third joint unit.

The first wire (not shown) and the second wire (not shown) are spaced apart in the Y direction, and each wire passes through the first to third joint units in the front-rear direction and causes the first to third joint units to bend.

According to this embodiment, the pair of elastic members on opposing sides (the first and second elastic members 91, 92, the second and third elastic members 93, 94, and the fifth and sixth elastic members 95, 96) have the same elastic coefficient. However, it is possible to vary the type of bending of the articulating structure 2' by changing the elastic coefficients of the first elastic member 91, the third elastic member 93 and the fifth elastic member 95.

The elastic coefficient of the elastic member according to this embodiment may be changed by changing the type of polymer.

In addition to these embodiments, the elastic member of the present disclosure is not limited to number, shape and arrangement if it elastically deforms by the pressing force by the rotation of the front segment of the joint unit of the articulating structure, and is balanced with the pressing force during the action of the pressing force (i.e., during the bending of the joint unit) to provide an elastic force that resists the pressing force.

It should be understood that a coil spring disposed concentrically with the lengthwise central axis of the joint unit between the front segment and the rear segment of the joint unit does not correspond to the elastic member of the present disclosure in terms of "a pressing force and an elastic force are balanced during the action of the pressing force by the rotation of the joint unit".

Due to the structure of the joint unit, when bending the joint unit using the wire, an eccentric load from the lengthwise central axis of the joint unit is applied to the corresponding coil spring. The coil spring subjected to the eccentric load from the central axis is a typical structure in which buckling occurs. Describing in more detail, when the eccentric load from the lengthwise central axis is applied to the coil spring, a non-uniform force is applied to the coil spring. Accordingly, when the pressing force reaches a specified value, the pressing force and the elastic force are unbalanced, and the coil spring suddenly bends on one side, resulting in collapse. During the action of the pressing force, the pressing force and the elastic force are unbalanced.

As described above, the coil spring disposed concentrically with the lengthwise central axis of the joint unit is not a structure free from buckling, and thus it is difficult to expect that the use of the corresponding structure as the elastic member will prevent buckling that occurs when the joint unit rotates.

What is claimed is:

1. An articulating structure, comprising:
    a joint unit including a front segment and a rear segment that are connected in series and perform relative rotation with respect to a rotation portion, and an elastic member interposed between the front segment and the rear segment; and
    a wire that passes through the front segment and the rear segment in a lengthwise direction of the joint unit,
    wherein the front segment rotates relative to the rear segment in one direction when the wire is pulled rearward, the elastic member elastically deforms by a pressing force by the rotation of the front segment to provide an elastic force that resists the pressing force, and the elastic force and the pressing force are balanced during the action of the pressing force, wherein a plurality of joint units is connected is series, wherein the elastic members of the plurality of joints units have same of different elastic coefficients.

2. The articulating structure according to claim 1, wherein the rear segment of a front joint unit becomes the front segment of a rear joint unit connected thereto.

3. The articulating structure according to claim 1, wherein the plurality of joint units includes a plurality of X direction joint units in which the front segment rotates relative to the rear segment in an X direction, and a plurality of Y direction joint units in which the front segment rotates relative to the rear segment in a Y direction perpendicular to the X direction.

4. The articulating structure according to claim 3, wherein the plurality of X direction joint units and the plurality of Y direction joint units are arranged in an alternating manner along the lengthwise direction.

5. The articulating structure according to claim 1, wherein the elastic member is a plate spring that bends by the pressing force of the front segment.

6. The articulating structure according to claim 5, wherein the rotation portion includes:

a rotation protrusion that is formed on a rear surface of the front segment, and has a rotation surface that forms part of a cylinder; and a rotation seat that is formed on a front surface of the rear segment, and supports the rotation protrusion.

7. The articulating structure according to claim 6, wherein the rear segment has a central groove that is recessed in the front surface, and the rotation seat is formed in the central groove, and the plate spring includes:

a connecting portion that is inserted into the central groove; and an elastic portion that is connected to the connecting portion, and extends obliquely toward the rear surface of the front segment outside of the central groove.

8. The articulating structure according to claim 7, wherein in an initial state in which the joint unit is placed in a straight line, the elastic portion in an unbent state comes into contact with the rear surface of the front segment.

9. The articulating structure according to claim 8, wherein comprises a plurality of wires that passes through the front segment and the rear segment in the lengthwise direction of the joint unit, the front segment rotates relative to the rear segment in one direction when a first wire is pulled rearward, the front segment rotates relative to the rear segment in the other direction opposite the one direction when a second wire in symmetry with the first wire with respect to a lengthwise central axis of the joint unit is pulled rearward, and the plate spring includes a first elastic portion formed on the one direction side and a second elastic portion formed on the other direction side.

10. The articulating structure according to claim 7, wherein the connecting portion is inserted between the rotation protrusion and the rotation seat.

11. The articulating structure according to claim 10, wherein the connecting portion includes:

a curved portion that forms a curve forming part of a cylinder, and is inserted between the rotation protrusion and the rotation seat; and a bent portion that is inserted between two rotation seats.

12. The articulating structure according to claim 7, wherein the elastic portion has a notch cut to allow the wire to pass therethrough.

13. The articulating structure according to claim 1, wherein the elastic member is a disc that is inserted into a gap between the front segment and the rear segment, and the disc is compressed by a pressing force by the rotation of the front segment to provide a force that resists the pressing force.

14. The articulating structure according to claim 13, wherein the front segment rotates relative to the rear segment in the one direction and the other direction opposite the one direction, the elastic member includes a first elastic member that is inserted into the one direction side and a second elastic member that is inserted into the other direction side, the first elastic member and the second elastic member are inserted into the gap between the front segment and the rear segment while being in a compressed state, and when the front segment rotates in one direction, the first elastic member is further compressed and resists the rotation of the front segment, and the second elastic member expands by a restoring force to help the front segment to rotate.

15. A tube inserting device, comprising:

an elongated tube; and an articulating structure connected to a front end of the tube, wherein the articulating structure is defined in claim 1.

16. The tube inserting device according to claim 15, wherein the rear segment of a front joint unit becomes the front segment of a rear joint unit connected thereto.

17. The tube inserting device according to claim 15, wherein the plurality of joint units includes a plurality of X direction joint units in which the front segment rotates relative to the rear segment in an X direction, and a plurality of Y direction joint units in which the front segment rotates relative to the rear segment in a Y direction perpendicular to the X direction.

18. The tube inserting device according to claim 17, wherein the plurality of X direction joint units and the plurality of Y direction joint units are arranged in an alternating manner along the lengthwise direction.

19. The tube inserting device according to claim 15, wherein the elastic member is a plate spring that bends by the pressing force of the front segment.

20. The tube inserting device according to claim 19, wherein the rotation portion includes:

a rotation protrusion that is formed on a rear surface of the front segment, and has a rotation surface that forms part of a cylinder; and a rotation seat that is formed on a front surface of the rear segment, and supports the rotation protrusion.

21. The tube inserting device according to claim 20, wherein the rear segment has a central groove that is recessed in the front surface, and the rotation seat is formed in the central groove, and the plate spring includes:

a connecting portion that is inserted into the central groove; and an elastic portion that is connected to the connecting portion, and extends obliquely toward the rear surface of the front segment outside of the central groove.

22. The tube inserting device according to claim 21, wherein in an initial state in which the joint unit is placed in a straight line, the elastic portion in an unbent state comes into contact with the rear surface of the front segment.

23. The tube inserting device according to claim 22, wherein comprises a plurality of wires that passes through the front segment and the rear segment in the lengthwise direction of the joint unit,
the front segment rotates relative to the rear segment in one direction when a first wire is pulled rearward,
the front segment rotates relative to the rear segment in the other direction opposite the one direction when a second wire in symmetry with the first wire with respect to a lengthwise central axis of the joint unit is pulled rearward, and
the plate spring includes a first elastic portion formed on the one direction side and a second elastic portion formed on the other direction side.

24. The tube inserting device according to claim 21, wherein the connecting portion is inserted between the rotation protrusion and the rotation seat.

25. The tube inserting device according to claim 24, wherein the connecting portion includes:
a curved portion that forms a curve forming part of a cylinder, and is inserted between the rotation protrusion and the rotation seat; and
a bent portion that is inserted between two rotation seats.

26. The tube inserting device according to claim 21, wherein the elastic portion has a notch cut to allow the wire to pass therethrough.

27. The tube inserting device according to claim 15, wherein the elastic member is a disc that is inserted into a gap between the front segment and the rear segment, and
the disc is compressed by a pressing force by the rotation of the front segment to provide a force that resists the pressing force.

28. The tube inserting device according to claim 27, wherein the front segment rotates relative to the rear segment in the one direction and the other direction opposite the one direction,
the elastic member includes a first elastic member that is inserted into the one direction side and a second elastic member that is inserted into the other direction side,
the first elastic member and the second elastic member are inserted into the gap between the front segment and the rear segment while being in a compressed state, and
when the front segment rotates in one direction, the first elastic member is further compressed and resists the rotation of the front segment, and the second elastic member expands by a restoring force to help the front segment to rotate.

29. An articulating structure, comprising:
a joint unit including a front segment and a rear segment that are connected in series and perform relative rotation with respect to a rotation portion, and an elastic member interposed between the front segment and the rear segment; and
a wire that passes through the front segment and the rear segment in a lengthwise direction of the joint unit,
wherein the front segment rotates relative to the rear segment in one direction when the wire is pulled rearward,
the elastic member elastically deforms by a pressing force by the rotation of the front segment to provide an elastic force that resists the pressing force, and
the elastic force and the pressing force are balanced during the action of the pressing force,
wherein a plurality of joint units is connected in series,
wherein the plurality of joint units includes a plurality of X direction joint units in which the front segment rotates relative to the rear segment in an X direction, and a plurality of Y direction joint units in which the front segment rotates relative to the rear segment in a Y direction perpendicular to the X direction.

30. A tube inserting device, comprising:
an elongated tube; and
an articulating structure connected to a front end of the tube, wherein the articulating structure is defined in claim 1.

* * * * *